United States Patent [19]

Nielsen et al.

[11] 4,356,312

[45] Oct. 26, 1982

[54] ETHYLENE OXIDE PROCESS

[75] Inventors: Robert P. Nielsen, Houston, Tex.; John H. La Rochelle, Baton Rouge, La.

[73] Assignee: Shell Oil Company, Houston, Tex.

[21] Appl. No.: 22,750

[22] Filed: Mar. 22, 1979

Related U.S. Application Data

[63] Continuation-in-part of Ser. No. 3,156, Jan. 15, 1979, abandoned, which is a continuation of Ser. No. 621,267, Oct. 10, 1975, abandoned, which is a continuation-in-part of Ser. No. 480,896, Jun. 19, 1974, abandoned, which is a continuation-in-part of Ser. No. 317,349, Dec. 21, 1972, abandoned, which is a continuation-in-part of Ser. No. 216,188, Jan. 7, 1972, abandoned.

[51] Int. Cl.³ .......................................... C07D 301/10
[52] U.S. Cl. .................................................... 549/534
[58] Field of Search .................................... 260/348.34

[56] References Cited

U.S. PATENT DOCUMENTS

| 3,132,157 | 5/1964 | Endler et al. | 260/348.34 |
| 3,647,720 | 3/1972 | Bryce-Smith et al. | 260/348.34 |
| 3,702,259 | 11/1972 | Nielsen | 260/348.34 |

*Primary Examiner*—Norma S. Millstone

[57] ABSTRACT

When supported silver materials are being prepared, deposits of from about $4.0 \times 10^{-5}$ to about $8.0 \times 10^{-3}$ gram equivalent weights per kilogram of finished product of ionic, higher alkali metals, i.e., ionic potassium, rubidium or cesium simultaneously with the deposit of silver improves the selectivity of these materials as catalysts for ethylene oxide production. Particularly good results are obtained with potassium.

25 Claims, 3 Drawing Figures

ETHYLENE OXIDE PROCESS

This application is a continuation-in-part of application, Ser. No. 3,156, filed Jan. 15, 1979, now abandoned, which is a continuation of application Ser. No. 621,267, filed Oct. 10, 1975, now abandoned, which is a continuation-in-part of application Ser. No. 480,896, filed June 19, 1974 now abandoned, which is a continuation-in-part of application Ser. No. 317,349 filed Dec. 21, 1972, now abandoned, which is a continuation-in-part of application Ser. No. 216,188, filed Jan. 7, 1972 now abandoned.

BACKGROUND OF THE INVENTION

1. Field of the Invention

This invention relates to improved silver catalysts for the production of ethylene oxide, their preparation, and their use in ethylene oxide processes.

2. The Prior Art

Materials consisting of silver upon supports are known to be useful catalysts for the production of ethylene oxide by the controlled incomplete oxidation of ethylene with molecular oxygen. A great variety of modifications have been proposed to improve the activity and selectivity of these catalysts. These modifications have involved, for example, the supports employed, the method of production, the physical form of the silver on the support and the addition of additives to the catalyst.

The alkali metals and their salts have been repeatedly proposed as additives for various silver ethylene oxide catalysts. Carter, in U.S. Pat. No. 2,125,333, issued Aug. 2, 1938, was among the first to disclose alkali metal addition. He specified the use of "small amounts" of alkali metals, including both sodium or potassium, in his silver catalyst. Later patents elaborated on this disclosure, but often with contradictory teachings. McNamee et al in U.S. Pat. No. 2,238,474, issued Apr. 15, 1941, disclosed that while 100 ppm by weight to 24% by weight of sodium improved silver catalysts, these amounts of potassium had a detrimental effect in catalyst performance. Sears, Jr. et al in U.S. Pat. No. 2,615,900, issued Oct. 29, 1952, cites a large number of promoters useful in broad weight ranges, but makes no distinction in the effectiveness of the various promoters. Saken, in U.S. Pat. No. 2,671,764, issued Mar. 9, 1954 disclosed the use of large amounts of alkali metal sulfates. Saken in U.S. Pat. No. 2,765,283, issued Oct. 2, 1956, proposed adding from 1 ppm by weight to 2000 ppm by weight of an inorganic chlorine compound to the catalyst support prior to the addition of silver to improve the finished catalysts. Saken's inorganic chlorine compounds included the alkali metal salts of chlorine acids, especially sodium chloride. Carlson et al in U.S. Pat. No. 2,773,844, issued Dec. 11, 1956 discloses a multistep silver deposition process but is not concerned with simultaneous deposition of alkali metals. Gould et al, in U.S. Pat. No. 2,799,687, issued July 16, 1957, disclosed that when from about 20 ppm by weight to about 1.6% by weight of inorganic halide (sodium chloride or preferably potassium chloride) are added as separate solid particles to a fluidized bed of supported silver catalyst, the halide acts as a suppressant, inhibiting the catalyst activity. Hosoda et al in U.S. Pat. No. 3,144,416, issued Aug. 11, 1964, cites a number of promoter materials, but gives no limits on their concentration. Kriger et al in U.S. Pat. No. 3,563,913 issued Feb. 16, 1971, generally discloses the use of alkali and alkaline earth metals as promoters, listing specifically lithium with no reference to cesium, rubidium or potassium. He notes that these promoters are preferably added to the catalyst support before the latter is impregnated with the silver compound containing solution. Long in U.S. Pat. No. 3,575,888, issued Apr. 20, 1971, disclosed the use of aluminum oxide supports having a pore volume between about 0.15 and 0.30 m²/gm and surface area below about 10 m²/gm. Nielson in U.S. Pat. No. 3,702,259, issued Nov. 7, 1972 uses certain organic amine solubilizing/reducing agents to produce uniformly spaced, adherent, hemispherical deposits of metallic silver on catalyst supports.

The prior art clearly recognizes that alkali metal compound addition changes, for better or worse, the character of a silver ethylene oxide catalyst. There is no recognition of real advantages for any special amounts of alkali metal addition, 1 ppm being considered the equivalent of 2000 ppm, for example. Moreover, there is no recognition of any special chemical advantages for the addition of certain alkali metals over other alkali metals. Further, there is no recognition that the simultaneous deposition of the alkali metal with the silver gives any special advantage over a sequential deposition scheme.

STATEMENT OF THE INVENTION

It has now been found that certain materials consisting essentially of silver deposited on a refractory support exhibit improved selectivity as catalysts for the partial oxidation of ethylene to ethylene oxide. These materials are formed when from about $4.0 \times 10^{-5}$ to about $8.0 \times 10^{-1}$ gram equivalent weights per kilogram (based on the entire catalyst weight) of ions of potassium, are deposited on the catalyst support coincidentally with the deposit of silver. It has also been found that when rubidium and cesium are similarly employed as claimd in applicants' patents U.S. Pat. No. 3,962,136 issued June 8, 1976 and U.S. Pat. No. 4,012,425 issued Mar. 3, 1977, they permit production of a catalyst of improved selectivity for the above mentioned reaction, but at different levels of selectivity than that obtainable with potassium-modified catalysts at otherwise comparable conditions. In contrast, it has been found that ions of the lower alkali metals, lithium, and sodium, fail to cause commercially significant improvement at these additions.

BRIEF DESCRIPTION OF THE DRAWINGS

FIG. 3 shows selectivity as a function of potassium content for a catalyst containing 11 percent silver. FIG. 1 was obtained with catalysts having 7.8 percent silver.

DETAILED DESCRIPTION OF THE INVENTION

The Catalyst of this Invention

When supported silver catalyst materials are prepared by the simultaneous deposition of potassium with the silver on the support material, a catalyst superior in selectivity for ethylene oxide production is produced.

Catalysts in accord with this invention comprise a porous refractory support having deposited on its exterior and interior (pore) surfaces from about 2% to about 20% by weight, based on total catalyst, of silver and certain amounts of ionic potassium. Mixtures of alkali metals may be employed and the use of minor proportions of rubidium, cesium, or mixtures thereof relative to potassium is within the compass of the present invention. For purposes of the present specification, the effective metals potassium, rubidium and cesium are referred to as "higher alkali metals" and potassium, the metal claimed herein, as "higher alkali metal of this invention".

The higher alkali metal of this invention is present on the catalysts in the form of its cation, rather than as the extremely active free alkali metals. Silver, on the other hand, is present on the finished catalysts as silver metal. The exact form of the alkali metal on the finished catalyst is not known. However, the heat treatment given to the impregnated support in order to reduce the silver salts to metallic silver will most likely convert the alkali metal salts to an oxide or oxidic compound. The exact form of this oxide compound has not been determined, but most likely it will depend upon the alkali metals present and the type of support used. By way of explanation and without intending to limit the scope of the invention, it is hypothesized that the oxide compound somehow forms a complex with the catalyst support surface rather than simply being deposited inertly upon the support surface. For example, when the alkali metal is deposited upon an alumina support it is thought that an aluminum-alkali metal-oxygen complex is formed. For sake of clarity in this specification and claims the amount of alkali metal oxide compound present on the catalyst support has been expressed as the gram equivalent weight of the alkali metal rather than the oxide. While the catalysts of this invention will have deposited on the support surface oxides or compounds of potassium, minor amounts of proportions of oxides or compounds of rubidium or cesium or mixtures of rubidium and cesium relative to potassium are within the compass of this invention. The alkali metal present in final form on the support in the form of an oxide or compound will be selected from the group consisting of potassium, potassium combined with a minor amount of rubidium, potassium combined with a minor amount of cesium or potassium combined with a minor amount of a mixture of rubidium and cesion, said minor amounts being relative of potassium. Alternatively stated, the alkali metal is present in final form on the support in the form of an oxide or oxide compound in which the said oxide or compound consists of the oxide or compound of potassium optionally combined with a minor amount of oxides or compounds of rubidium or cesium or mixtures of rubidium and cesium oxides or compounds relative to said potassium.

The amount of the higher alkali metal (or metals) present on the catalyst surface is critical. For the higher alkali metal of this invention, it appears that amounts of less than about $4.0 \times 10^{-5}$ gram equivalent weights (gew) per kilogram or greater than about $8.0 \times 10^{-3}$ gew per kilogram provide no significant improvement. The amount of higher alkali metal of this invention present on the catalyst preferably ranges from about $2.0 \times 10^{-4}$ to about $6.5 \times 10^{-3}$ gew per kilogram of finished catalyst. As is more specifically detailed below, the amount of higher alkali metal required for this invention is a function of the surface area of the catalyst. Thus, the amount of higher metal of this invention desirably present will fall at the higher limit of the desired range for the higher surface area supports and at the lower limit for the lower surface area supports of this invention. Below about 0.8 m²/g a desired range of alkali metals of this invention is from about $0.3 \times 10^{-3}$ to about $3.2 \times 10^{-3}$ gew per kilogram of finished catalyst and more preferably between about $0.35 \times 10^{-3}$ to about $3 \times 10^{-3}$ gew per kilogram of finished catalyst and even more preferably between about $5.0 \times 10^{-4}$ to about $2.4 \times 10^{-3}$ and most preferably between about $7.5 \times 10^{-4}$ to about $2.3 \times 10^{-3}$ gew per kilogram of finished catalyst. The original application Ser. No. 26,188, filed Jan. 7, 1972, now abandoned, disclosed a range of higher alkali metals of from about $0.5 \times 10^{-3}$ to about $2.4 \times 10^{-3}$ gew per kilogram of finished catalyst and preferably from about $0.75 \times 10^{-3}$ to about $2.3 \times 10^{-3}$ gew per kilogram of finished catalyst. Other undetermined experimental factors or other unknown variables may also contribute to minor variations in the concentration range of the higher alkali metal of this invention wherein optimum selectivity is obtained when the catalysts are employed in partial oxidation of ethylene to ethylene oxide.

It must be made clear that the amount of potassium simultaneously deposited is not necessarily the total amount of this metal present in the catalysts. It is the amount of this alkali metal which is present on the surface of the catalyst and which is intentionally added to the catalysts coincidentally with the addition of silver. It is not unusual for substantial amounts, often up to about 10,000 ppm wt. of an alkali metal (usually potassium) to be present within the porous support due to use of support materials containing naturally occuring alkali metals or inadvertent alkali metal addition during support manufacture. These amounts of alkali metal present in the support in non-leachable form, rather than on the surface coincidentally added with the silver, do not appear to contribute to the improved performance of catalysts in accord with this invention and are neglected in determination of alkali metal concentrations.

Catalyst according to this invention preferably contain from about 2% to about 20% by weight based on the total catalyst of silver as silver metal. Preferably they contain from about 3 to about 15 percent and most preferably from about 4% to about 13% by weight of silver. The use of larger amounts of silver is not excluded but is generally economically unattractive. The silver is deposited over the interior and exterior surfaces of the catalyst support and should be evenly dispersed over these surfaces.

The exact physical form of the silver upon the support can vary and does not appear to be critical to the invention. Very excellent results are obtained with the controlled surface alkali metal content catalyst of this invention, however, when the silver is present in the form of uniformly spaced, discontinuous, adherent, substantially hemispherical, discrete particles having a uniform diameter of less than one micron (10,000 Å). Best results are obtained with this type of catalyst when the silver particles have diameters of from about 1000 to about 10,000 Å and most preferred catalysts have silver particles of an average diameter in the range of from about 1500 to about 7500 Å.

The support employed in these catalysts in its broadest aspects is selected from the larger number of conventional, porous, refractory catalyst carriers or support materials which are essentially inert in the presence of the ethylene oxidation feeds, products and reaction conditions. Such conventional materials may be of natural or synthetic origin and preferably are of a macroporous structure, that is, a structure having a surface area below about 10 m$^2$/g and preferably below about 2 m$^2$/g. These support materials typically have an apparent porosity of greater than 20%. Very suitable supports comprise those of siliceous and/or aluminous composition. Specific examples of suitable supports are the aluminum oxides (including the materials sold under the trade name "Alundum"), charcoal, pumic, magnesia, zirconia, kieselguhr, fuller's earth, silicon carbide, porous agglomerates comprising silicon and/or silicon carbide, silica, magnesium, selected clays, artificial and natural zeolites and ceramics. Refractory supports particularly useful in preparation of catalyst in accordance with this invention comprise the aluminous materials, in particular those containing alpha alumina. In the case of alpha alumina-containing supports, preference is given to those having a specific surface area as measured by the B.E.T. method of from about 0.03 m$^2$/g to about 2.0 m$^2$/g and an apparent porosity as measured by conventional mercury or water absorption techniques of from about 25% to about 50% by volume. The B.E.T. method for determining specific surface area is described in detail in Brunauer, S., Emmet, P. H. and Teller, E., *J. Am. Chem. Soc.*, 60, 309–16 (1938).

When certain types of alpha alumina-containing supports are employed, the advantages of the special alkali metal addition of this invention are especially emphasized. These alpha alumina supports have relatively uniform pore diameters and are more fully characterized by having (1) B.E.T. specific surface areas of from about 0.1 m$^2$/g to about 2.0 m$^2$/g, preferably about 0.1 m$^2$/g to about 0.8 m$^2$/g and (2) apparent porosities of from about 42% to about 56%, preferably from about 46% to about 52%. Specific examples of these most advantageous supports are the supports marketed by Norton Company as "Alundum" grades LA-956, LA-5556 and LA-4118. Further details on these supports are given in Table I.

TABLE I

| Support | LA-956 | LA-5556 | LA-4118 |
|---|---|---|---|
| Surface Area, m$^2$/g | .17 | .24 | .35 |
| Specific Pore Volume, cc/g | .19 | .25 | .31 |
| Median Pore Diameter, Microns | 2.5 | 4.4 | 5.7 |
| % of Pores between 1.5 and 15 Microns | 79 | 81 | 47 |

When these types of alumina are used, it has been found that the amount of higher alkali metal simultaneously deposited with the silver needed for optimum selectivity to ethylene oxide is directly related to the surface area of the support. For example, if the ratio of the cesium value at maximum selectivity to B.E.T. surface area is calculated, a value of about $$\frac{5 \times 10^{-3} \text{ gew per kilogram of finished catalyst}}{m^2/g}$$

is obtained. A somewhat higher rate is obtained for potassium. While the scientific explanation for the above mentioned relationship between the support surface area and the selectivity is not understood, it is expected that similar relationships will hold for any of the other large number of conventional porous catalyst supports used to prepare the catalysts of this invention.

Regardless of the character of the support used, it is preferably shaped into particles, chunks, pieces, pellets, rings, spheres, and the like of a size suitable for employment in fixed bed applications. Conventional commercial fixed bed ethylene oxidation reactors are typically in the form of a plurality of parallel elongated tubes (in a suitable shell) approximately 1 to 2 inches in diameter and 24 to 45 feet long filled with catalyst. In such reactors, it is desirable to employ a support formed into a rounded shape, such as for example, spheres, pellets, rings, tablets, and the like, having diameters of from about 0.1 inch to about 0.8 inch.

The Catalyst Preparation

The catalysts of this invention are prepared by a technique which causes the coincidental deposit of silver and the desired alkali metal upon the catalyst support surfaces.

A great variety of methods for adding silver to supports are known. In a typical method, the support may be impregnated with an aqueous solution of silver nitrate, dried, and the silver reduced with hydrogen or hydrazine as described in U.S. Pat. No. 3,575,888, issued Apr. 20, 1971, to Long. In another technique the support may be impregnated with an ammoniacal solution of silver oxalate or carbonate and the silver metal formed by thermally decomposing the salts. Silver may be added as well by the technique disclosed in U.S. Pat. No. 3,702,259 of Nielsen, wherein the support is impregnated with special aqueous solution so silver salts and combinations of ammonia, vicinal alkanolamines and vicinal alkyldiamines and then thermally treated. Other possible methods for adding silver include impregnating a support with an ethanolamine-containing solution of silver salt and then reducing, as disclosed by Japanese Pat. No. 19606/1971, or by adding a slurry of fine particles of silver carbonate to the support and thermally decomposing as described by Endler in U.S. Pat. No. 3,043,854 issued July 10, 1962. In each of these techniques, silver is added to the support when the support is contacted with a liquid phase, either a silver solution or a slurry of silver particles. With these techniques, an excellent method for adding the desired alkali metals which enable their simultaneous deposit with silver is to dissolve them as suitable salts in this liquid phase in an amount regulated to give the required alkali metal addition to the finished catalyst when the support is contacted therewith. Suitable higher alkali metal salts generally include all those which are soluble in the silver-depositing liquid phase. In this regard, no unusual effectiveness is observed with use of any particular anion in the alkali metal salts. For example, nitrates, nitrites, chlorides, iodides, bromates, bicarbonates, oxalates, acetates, tartrates, lactates, isopropoxides, and similar common alkali metal salts may be used. However, alkali metal salts should be avoided which react with the silver present in the liquid phase such as to cause silver salts to precipitate prematurely out of an impregnating solution. For example, potassium chloride should not be used in impregnation techniques which use an aqueous silver nitrate solution but can be used in such a technique with an aqueous solution of silver amine complexes from which silver chloride will not precipitate.

In general terms, catalysts in accord with this invention are prepared by (a) contacting a suitable solid porous refractory support with a liquid phase which contains an amount of silver, either as silver compounds dissolved in the liquid phase or as a slurry of silver compound particles, in an amount sufficient to deposit from 2 to 20% by weight of silver on the support surface and an amount of dissolved salts of potassium optionally combined with a minor amount of salts of rubidium, cesium or mixtures of rubidium and cesium salts relative to said potassium salts sufficient to deposit from $4.0 \times 10^{-5}$ to $8.0 \times 10^{-3}$ gew per kilogram of these higher alkali metals as salts on the surface of the support, thereby coincidentally depositing these amounts of silver compounds and alkali metal salts upon the catalyst surface; and (b) thermally treating the resulting silver compound and higher alkali metal salt-containing product in the presence of a reducing agent to convert the silver compound to silver metal. Suitable impregnating solutions contain, for example, from about 3 to about 40% by weight of silver salts and from about 25 to about 500 ppm by weight of alkali metal. The exact concentrations employed generally may require some routine experimentation since the amount of alkali metal deposited from a solution, which is critical, will depend in part on the porosity of the catalyst support. However, methods of varying the amount of silver and/or alkali metal deposited are conventional, as is the analytical determination of the amount of the materials actually deposited.

Also within the scope of the invention is an alternative method of coincidentally depositing the silver and higher alkali metal salt on the support surface which provides a ready means of controlling the amount of higher alkali metal deposited within the limits of the invention, i.e., $4.0 \times 10^{-5}$ to $8.0 \times 10^{-3}$ gew per kilogram of finished catalyst. This method involves deposition of larger than required amounts of the higher alkali metal, that is, in excess of $8.0 \times 10^{-3}$ gew per kilogram of finished catalyst, coincidentally with the silver according to the general procedure described above followed by contacting the catalyst particles so prepared with an anhydrous alkanol of 1 or 2 carbon atoms. The higher alkali metals contemplated by this invention are soluble in the alkanol solvents described to a sufficient degree that one or more washings with the alkanol solvents will selectively remove the excess coincidentally deposited higher alkali metal such that the amount remaining intact on the support surface falls within the concentration range critical to the invention. This method then provides a ready means of adjusting the higher alkali metal concentration from levels in excess of this described by the invention, whether the result of purposeful or inadvertent actions, to specific concentrations within the limits of the invention, by a process which is readily applicable to large plant scale operations.

The alkali metal addition of this invention is especially effective when used in conjunction with silver catalyst preparation techniques wherein silver is added to the support from a basic solution, particularly from a nitrogeneous base-containing basic solution. Examples of these nitrogenous bases are ammonia, the alkylamines and the alkanolamines.

Thus, in a preferred embodiment, catalysts of this invention are prepared by (a) adding to a porous aluminous support from about 3% by weight to about 15% by weight of silver in the form of water-soluble silver salts and from about $1.0 \times 10^{-4}$ gew per kilogram to about $6.5 \times 10^{-3}$ gew per kilogram of higher alkali metal of this invention (potassium) in the form of water-soluble salts by contacting the support with an alkaline aqueous solution of the silver and alkali metal salts; and (b) maintaining the product of step (a) at a temperature of from about 100° C. to about 500° C. in the presence of a reducing agent for a period sufficient to convert the silver salts to silver metal.

In a particularly preferred modification, the alkali metal addition of this invention is used in conjunction with catalyst preparation techniques such as those disclosed in U.S. Pat. No. 3,702,259 of Nielsen. This preferred preparation method involves impregnation of an alumina support with certain aqueous alkali metal silver salt solutions and a subsequent thermal reduction of the silver salt. The impregnation solution consists essentially of:

A. a silver salt of a carboxylic acid,
B. an organic amine alkaline solubilizing/reducing agent,
C. a salt of potassium, and
D. an aqueous solvent.

Suitable carboxylic acid silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution used in this preparation method. Suitable organic amine silver-solubilizing/reducing agents include lower alkylenediamines of from 1 to 5 carbon atoms, mixture of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are preferred. They are the following:

A. vicinal alkylenediamines of from 2 to 4 carbon atoms;
B. mixtures of (1) vicinal alkanolamines of from 2 to 4 carbon atoms and (2) vicinal alkylenediamines of from 2 to 4 carbon atoms;
C. mixtures of vicinal alkylenediamines of from 2 to 4 carbon atoms and ammonia; and
D. mixtures of vicinal alkanolamines of from 2 to 4 carbon atoms and ammonia.

These preferred solubilizing/reducing agents are generally added in the amount of from 0.1 to 10 moles per mole of silver present.

Very preferred as solubilizing/reducing agents are:
A. ethylenediamine,
B. ethylenediamine in combination with ethanolamine,
C. ethylenediamine in combination with ammonia, and
D. ethanolamine in combination with ammonia.

Ethylenediamine in combination with ethanolamine is more preferred.

When ethylenediamine is used as the sole solubilizing/reducing agent, it is necessary to add amounts of the amine in the range of from 0.1 to 5.0 moles of ethylenediamine per mole of silver.

When ethylenediamine and ethanolamine together are used as solubilizing reducing agent, it is suitable to employ from 0.1 to 3.0 moles of ethylenediamine per mole of silver and from 0.1 to 2.0 moles of ethanolamine per mole of silver.

Suitable higher alkali metal salts are those of inorganic and organic carboxylic acids. It is often convenient to employ as the higher alkali metal salt the carboxylic acid salt corresponding to the silver carboxylate used, as for example to use potassium oxalate when silver oxalate is the silver source.

As already noted, it is essential that only certain controlled amounts of the higher alkali metal of this invention be present. These amounts are achieved by either controlled addition of alkali metal to an alkali metal-free silver solution or by controlled removal of alkali metal from the support surface after deposition of larger than required amounts of alkali metal. For example, a potassium-containing silver oxalate solution can be prepared by two methods. Silver oxide can be reacted with mixture of ethylenediamine and oxalic acid to yield a solution of silver oxalate ethylenediamine complex to which is then optionally added other amines, such as ethanolamine and controlled amounts of potassium. Alternatively, silver oxalate can be precipitated from potassium oxalate and silver nitrate and then repeatedly rinsed to remove adhered potassium salts until the desired potassium content is reached. The potassium-containing silver oxalate is then solubilized with ammonia and/or amines. When the support is contacted with these solutions, silver (as salts) and higher alkali metals (as salts) deposit simultaneously upon the support surfaces.

Subsequent to the use of any of these methods, the impregnated support is then heated at a temperature of from 100° to 375°, preferably from 125° to 325° C., for the time, typically ½ to 8 hours, required to decompose the silver salt and form the adherent particulate deposit of metallic silver on the surfaces. Lower temperatures do not adequately decompose the silver salt and should be avoided. More than one temperature may be employed.

In one special embodiment a silver oxalate-ethylenediamine complex solution containing larger than required amounts of alkali metal can be employed. In this case the concentration of alkali metal is reduced, after deposition on the support and subsequent thermal treatment to convert the silver compound to metallic silver by contacting the supported catalyst with a lower alkanol, i.e., methanol or ethanol, according to the general procedure described above.

Ethylene Oxide Production

The higher alkali metal-promoted silver catalysts have been shown to be particularly selective catalysts in the direct oxidation of ethylene with molecular oxygen to ethylene oxide. The conditions for carrying out such an oxidation reaction in the presence of the silver catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenol compounds, the desirability of employing recycle operations or applying successive conversion in different reactors to increase the yields of ethylene oxide, and any other special conditions which may be selected in processes for preparing ethylene oxide. Pressures in the range of from about atmospheric to about 500 psi are generally employed. Higher pressures may, however, be employed within the scope of the invention. Molecular oxygen employed as reactant is obtained from conventional sources. The suitable oxygen charge may consist essentially of relatively pure oxygen, a concentrated oxygen stream comprising oxygen in major amounts with lesser amounts of one or more diluent such as nitrogen, argon, etc., or another oxygen-containing stream such as air. The use of the present novel silver catalysts in ethylene oxidation reactions is in no way limited to the use of specific conditions among those which are known to be effective.

In a preferred application of the silver catalysts of the invention, ethylene oxide is produced when an oxygen-containing gas of not less than 95% oxygen is contacted with ethylene in the presence of the present catalysts at a temperature in the range of from 210° C. to 285° C. and preferably 225° C. to 270° C.

The resulting ethylene oxide is separated and recovered from the reaction product by conventional methods known and used in the art. Use of the silver catalysts of the invention in ethylene oxide production processes gives higher overall ethylene oxidation selectivities to ethylene oxide at a given ethylene conversion than are possible with conventional catalysts.

While the reason for these higher selectivities observed with catalysts of this invention is not fully understood, experiments have indicated with conventional silver catalysts (not containing higher alkali metals) cause ethylene oxide to combust after formation while silver catalysts containing from about $4.0 \times 10^{-5}$ to about $8.0 \times 10^{-3}$ gew per kilogram of codeposited higher alkali metal do not cause as extensive ethylene oxide combustion.

Preparation of catalysts according to the invention and their use in the production of ethylene oxide will be further described by the following examples which are provided for illustration and are not to be construed as limiting the invention.

Illustrative Embodiment I

Part A. A potassium-containing catalyst (Catalyst A) was prepared. As support for this catalyst was employed 5/16-inch diameter rings of alpha-alumina. This support contained 99.3% by weight alpha-alumina, 0.4% silica, and 0.3% of other metal oxides and had a surface area of 0.24 m²/g and an apparent porosity of 48–49% by volume. This support had a median pore diameter of 4.4 microns as determined by mercury porosimetry. Eighty percent of its pores had diameters in the range of from 1.5 to 15 microns. The tradename of this support was Norton Company's "Alundum", type LA-5556.

The support was impregnated with an aqueous solution of silver salt containing a controlled amount of potassium. Reagent grade silver oxide was mixed with an aqueous solution of reagent grade oxalic acid dissolved in ethylenediamine to form an about 2 molar solution of $Ag_2(EN)_2C_2O_4$. Ten percent by volume of ethanolamine (about 0.4 moles of ethanolamine per mole of silver) was then added to complete the solubilizing/reducing agent combination. This solution contained about 22% by weight silver. Potassium nitrate, to achieve 190 ppm weight of potassium, was added to the solution. The catalyst support was impregnated with this potassium-containing silver solution, vacuum being applied to ensure complete saturation. Excess liquid was drained off and the support was immediately placed in a forced air oven at 290° C. to dry the catalyst and reduce the silver salt to silver metal. Total heating time was about 3 hours. The silver content of the catalyst was determined to be 7.8% by weight and the potassium present on the catalyst surface was found to be 60 ppm (0.0015 gew of potassium per kilogram of catalyst).

The form of the silver deposits on the catalyst was examined by electron microscope and found to be discrete particles having a uniform diameter of from 0.2 to 0.4 microns (2000 to 4000 Å). These particles were uniformly spaced on the interior and exterior of the support. Repeated dropping and shaking of catalyst A showed that the silver particles were tightly adherent to the support surface.

Part B. For purposes of comparison, the preparation of part A was repeated with the difference that no alkali metal salt was added to the impregnating solution. Analysis verified that no more than 5 ppm of potassium was present in the solution. This catalyst (catalyst A') contained 7.8% by weight of silver.

Part C. The potassium-modified catalyst (catalyst A) and the alkali metal-free catalyst not in accordance with the invention (catalyst A') were comparatively tested as catalysts for production of ethylene oxide. In a representative experiment, 5/16-inch rings of catalyst A were crushed and 3.5 grams of 30/40 mesh particles of crushed catalyst were charged to a 0.20-inch diameter by 5-inch long reaction tube. A mixture of air and ethylene was passed over the catalyst in the presence of a chlorine-containing moderator at the following reaction conditions:

| | |
|---|---|
| Pressure, psig | 200 |
| Space Velocity, hours$^{-1}$ | 3300 |
| Ethylene/O$_2$ ratio | 3.75 |
| Moderator Concentration, ppm of Equivalent Chlorine | 10–15 |

The reaction temperature was adjusted to provide an oxygen conversion of 52% and the selectivity to ethylene oxide was determined. With catalyst A, a temperature of 253° C. was required to reach a standard oxygen conversion (52%). Selectivity to ethylene oxide was 78%. By comparison, the catalyst not in accordance with the invention (catalyst A') achieved a selectivity of only 69%.

Illustrative Embodiment II

A second potassium-containing, catalyst (catalyst B) was prepared using a method similar to the method of Illustrative Embodiment I, part A. The support of Illustrative Embodiment I was used.

This support was impregnated as in Illustrative Embodiment I with an aqueous solution of potassium and silver salts, which in this Example was prepared by the following different technique. An aqueous solution of reagent grade silver nitrate was mixed with stirring with an aqueous solution of reagent grade potassium oxalate. Silver oxalate precipitate was collected and washed repeatedly with deionized water until a potassium content of 8 ppm potassium per percent weight silver was noted. This potassium-containing silver oxalate was then dissolved in aqueous ethylenediamine and used to impregnate the support as in Example I. The finished catalyst contained 7.8% by weight of silver and 62 ppm by weight of coincidentally-deposited potassium. When catalyst B was employed as an ethylene oxide catalyst in accord with Illustrative Embodiment I, it gave standard conversion at 253° C. and 78.6% selectivity.

Illustrative Embodiment III

Using the general catalyst preparation technique, support and feedstocks of Illustrative Embodiment I, a group of silver catalysts were prepared having varying potassium contents. The compositions of the catalysts are listed in Table II.

The supports were impregnated as in Illustrative Embodiment I with an aqueous solution of potassium and silver salts, which in this example were prepared by the following different technique. An aqueous solution of reagent grade silver nitrate was mixed with stirring with an aqueous solution of reagent grade potassium oxalate. Silver oxalate precipitate was collected and washed repeatedly with deionized water until a potassium content adequate to produce the desired potassium content in the final product was noted. This potassium-containing silver oxalate was then dissolved in aqueous ethylenediamine, then monoethanolamine (10% by volume) was added and the resulting solution was used to impregnate the support as in Illustrative Embodiment I.

The finished catalyst contained 7.8% by weight of silver. These catalysts were tested as ethylene oxidation catalysts using the equipment and technique of Illustrative Embodiment I, part C. The results are shown in Table II and are plotted in FIG. 1.

TABLE II

| Catalyst | Added Potassium Content | | Oxidation Selectivity to Ethylene Oxide, $S_{52}$, % |
|---|---|---|---|
| | Gew of Potassium per Kilogram of Catalyst | Ppm wt. potassium | |
| 2-A | 0.00046 | 18 | 72.5 |
| 2-B | 0.00072 | 28 | 74.2 |
| 2-C | 0.00095 | 37 | 74.8 |
| 2-D | 0.0012 | 47 | 77.6 |
| 2-E | 0.0015 | 57 | 78.0 |
| 2-F | 0.0017 | 68 | 77.3 |
| 2-G | 0.0026 | 100 | 69.4 |

Illustrative Embodiment IV

Using the general catalyst preparation techniques, support and feedstocks of Illustrative Embodiment I, a group of silver catalysts were prepared having varying potassium contents. The compositions of the catalysts are listed in table III.

The supports were impregnated as in Illustrative Embodiment I with an aqueous solution of potassium and silver salts, which in the example were prepared by the following different technique. An aqueous solution of reagent grade silver nitrate was mixed with stirring with an aqueous solution of reagent grade sodium hydroxide. The resulting silver hydroxide precipitate was washed repeatedly with deionized water to remove as much sodium nitrate as possible. Oxalic acid dihydrate was added to provide ½ mole of acid for each mole of silver. The silver oxalate was then dissolved in aqueous ethylenediamine, then monoethanolamine (10% by volume) was added. The resulting solution was doped to the appropriate level by adding potassium nitrate.

Figure 1:
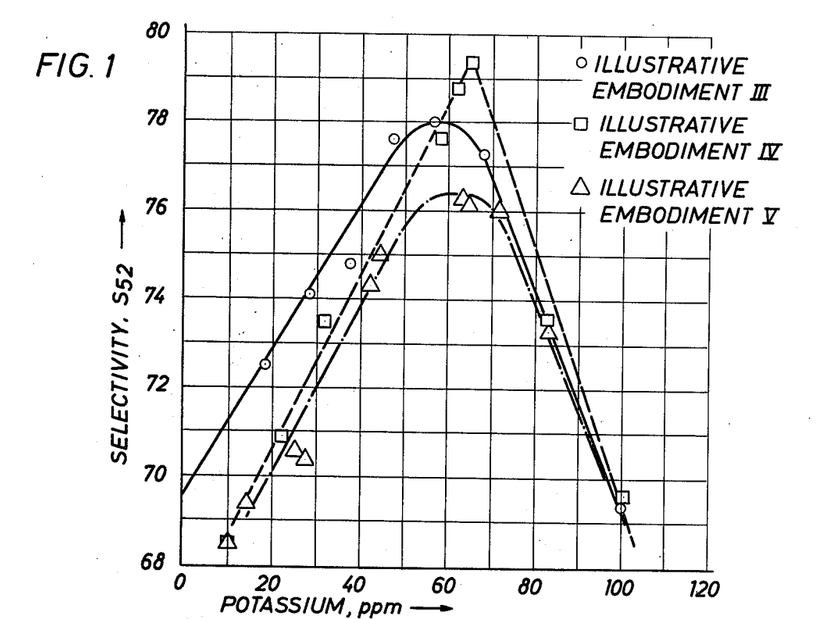
FIG. 1 shows the selectivity to ethylene oxide at 52 percent oxygen conversion for various concentrations of potassium on the catalyst. In this figure the same support was utilized, but different methods of preparing the silver-potassium impregnating solutions were used.

The finished catalyst contained 7.8% by weight of silver. The catalysts were tested as ethylene oxidation catalysts using the equipment and technique of Illustrative Embodiment I, part C. The results are shown in Table III and are plotted in FIG. I.

TABLE III

| Catalyst | Added Potassium Content | | Oxidation Selectivity to Ethylene Oxide, $S_{52}$, % |
|---|---|---|---|
| | Gew of Potassium per Kilogram of Catalyst | Ppm wt. potassium | |
| 3-A | 0.00026 | 10 | 68.5 |
| 3-B | 0.00056 | 22 | 70.9 |
| 3-C | 0.00085 | 33 | 73.5 |
| 3-D | 0.0015 | 58 | 77.7 |
| 3-E | 0.0016 | 62 | 78.8 |
| 3-F | 0.0017 | 65 | 79.4 |
| 3-G | 0.0021 | 82 | 73.6 |
| 3-H | 0.0026 | 101 | 69.5 |

Illustrative Embodiment V

A. Using the general catalyst preparation technique, support and feedstocks of Illustrative Embodiment I, a group of silver catalysts were prepared having varying potassium contents. These catalysts contained 7.8±0.3 percent by weight of silver.

Each of these catalysts was subjected to a prolonged test in a pilot scale ethylene oxide reactor 1¾ inches in diameter and 35 feet long.

The conditions of these experiments were as follows:

| | |
|---|---|
| Pressure, psig | 210 |
| Temperature, °C. | 245-260 |
| Space velocity, hours$^{-1}$ | 3300 |
| Ethylene in feed, % | 30 |
| Ethylene/O$_2$ ratio | 3.5 |
| Oxygen conversion, % | 52 |
| Optimum moderator concentration ppm of equivalent chlorine | 11-14 |

The results of these experiments are given in Table IV and plotted in FIG. 1.

TABLE IV

| Catalyst | Added Potassium Content | | Oxidation Selectivity to Ethylene Oxide, $S_{52}$, % |
|---|---|---|---|
| | Gew of Potassium per Kilogram of Catalyst | Ppm wt. Potassium | |
| 4-A | 0.00026 | 10 | 68.5 |
| 4-B | 0.00037 | 14 | 69.4 |
| 4-C | 0.00062 | 24 | 70.6 |
| 4-D | 0.00065 | 27 | 70.4 |
| 4-E | 0.0011 | 42 | 74.3 |
| 4-F | 0.0012 | 44 | 75.0 |
| 4-G | 0.0016 | 63 | 76.3 |
| 4-H | 0.0016 | 64 | 76.2 |
| 4-I | 0.0018 | 72 | 76.0 |
| 4-J | 0.0021 | 82 | 73.3 |

Illustrative Embodiment VI

Figure 2:
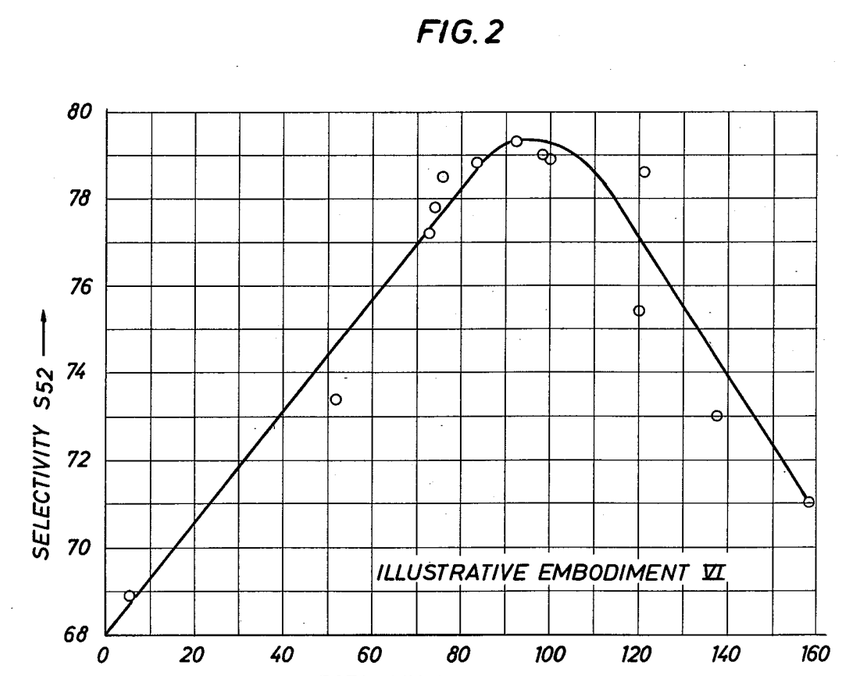
FIG. 2 shows selectivity as a function of potassium content for a support similar to the support used in FIG. 1 but prepared by a different manufacturer with an alpha aluminum from a different source. A slight shifting of the optimum to higher potassium levels is noted.

Using the general catalyst preparation technique of Illustrative Embodiment III a group of silver catalysts were prepared having varying potassium contents. The support utilized was an alpha-alumina support (99+alpha-alumina) supplied by carborundum company. It had a surface area of about 0.21 m$^2$/g, a pore volume of about 0.26 cc/gm, an apparent porosity of about 48-49% by volume, a median pore diameter of about 3.3-45 microns as determined by mercury porosimetry. The finished catalysts contain 7.6±3% by weight of silver. The catalysts were tested as ethylene oxide catalysts using the equipment and technique of Illustrative Embodiment I, part C, (3300 GHSV, 210 psig, 30% ethylene, 8.5% oxygen, 10 ppm vinyl chloride monomer in feed). The results are shown in Table V and are plotted in FIG. 2. The shift in optimum concentration of potassium to higher levels as compared to the Norton Catalysts above is thought to be due to differences in the types of alpha-alumina used in the manufacture of the support.

TABLE V

| Catalyst | Added Potassium Content | | Selectivity to Ethylene Oxide, $S_{52}$, % | Reactor Temp. at 52% O$_2$ Conversion |
|---|---|---|---|---|
| | Gew of Potassium Per Kilogram of Catalyst | Ppm wt. Potassium | | |
| 5-A | 0.00014 | 5.6 | 68.9 | 254° C. |
| 5-B | 0.0013 | 51 | 73.4 | 242 |
| 5-C | 0.0019 | 73 | 77.2 | 244 |
| 5-D | 0.0119 | 74 | 77.8 | 244 |
| 5-E | 0.0019 | 76 | 78.5 | 245 |
| 5-F | 0.0022 | 84 | 78.8 | 249 |
| 5-G | 0.0024 | 93 | 79.3 | 251 |
| 5-H | 0.0025 | 99 | 79.0 | 247 |
| 5-I | 0.0026 | 100 | 78.9 | 247 |
| 5-J | 0.0031 | 120 | 75.4 | 277 |
| 5-K | 0.0031 | 121 | 78.6 | 251 |
| 5-L | 0.0035 | 137 | 73.0 | 278 |
| 5-M | 0.0041 | 158 | 71.0 | 257 |

Illustrative Embodiment VII

Two series of catalysts were prepared using the feedstocks and general preparation method of Illustrative Embodiment I with the exception that in one series varying amounts of sodium were employed as dopant and in the other series varying amounts of lithium were used.

These catalysts all contained about 7.8% by weight silver and from 0.001 to 0.002 gew per kilogram of catalyst of lithium or sodium.

These catalysts were tested as ethylene oxidation catalysts using the equipment and technique of Example I, part C. Within the limits of experimental error, no improvement in selectively was noted with these catalysts.

Illustrative Embodiment VIII

Catalysts with differing silver contents and containing varying amounts of potassium as the higher alkali metal component were prepared using the feedstocks and general preparation technique of Illustrative Embodiment I. The support was the same as that used in Illustrative Embodiment I, part A. The catalyst compositions, so prepared, were tested as ethylene oxide catalysts using the apparatus and techniques of Illustrative Embodiment 1, part C. The compositions of these catalysts along with results of the ethylene oxide preparations utilizing these catalysts are summarized in Table VI below for the alkali metal concentrations giving the maximum selectivity at a given silver loading. The maximum selectivity for each silver loading was determined by, for example, a procedure such as that of Illustrative Embodiment V.

TABLE VI

| Catalyst | Silver Content % w | Added Potassium Content at Maximum Selectivity | | Reactor Temperature to Achieve 52% O$_2$ Conversion °C. | Oxidation Selectivity to Ethylene Oxide |
|---|---|---|---|---|---|
| | | Gew per Kilogram | Ppm wt. Potassium | | |
| 6-A | 4.1 | 0.00109 | 43 | 262.2 | 78.8 |
| 6-B | 7.8 | 0.00166 | 65 | 253.5 | 79.0 |
| 6-C | 10.4 | 0.00266 | 104 | 256.0 | 79.2 |

Illustrative Embodiment IX

Using the general catalyst preparation technique and feedstock of Illustrative Embodiment I, a group of silver catalysts were prepared with varying potassium contents. The support utilized was made by Norton and having the same specification as LA-5556 but utilizing a different source of alpha alumina.

The supports were impregnated as in Illustrative Embodiment I with an aqueous solution of potassium and silver salts, which in this example were prepared by the following different technique. An aqueous solution of reagent grade silver nitrate was mixed with stirring with an aqueous solution of reagent grade sodium hydroxide. The resulting silver hydroxide precipitate was washed repeatedly with deionized water to remove as much sodium as possible. Oxalic acid dihydrate was added to provide ½ mole of acid for each mole of silver. The silver oxalate precipitate was washed thoroughly with deionized water and was then dissolved in ethylene diamine. The resulting solution was doped to the appropriate level by adding potassium nitrate. The finished catalysts contain 11.0% silver.

Figure 3:
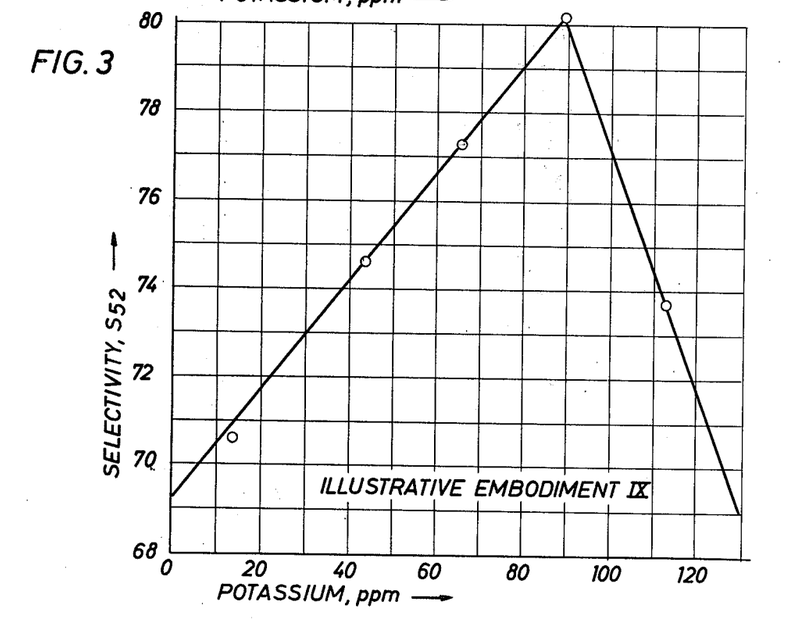

The catalysts were tested by using 3 grams of 14/20 mesh crushed catalyst in ¼" o.d. thin wall stainless steel reactors. Test conditions were 210 psig, 3300 GHSV, 8.5% O$_2$, 30% ethylene and 10–12 ppm vinyl chloride moderator. Selectivities were measured at 52% oxygen conversion. Results are shown in Table VII and are plotted in FIG. 3.

TABLE VII

| Catalyst | Added Potassium Content | | Selectivity to Ethylene Oxide, S$_{52}$ % | Reactor Time at 52% O$_2$ Conversion |
|---|---|---|---|---|
| | Gew of Potassium per Kilogram of Catalyst | Ppm wt. Potassium | | |
| 7-A | 0.00036 | 14 | 70.6 | 244° C. |
| 7-B | 0.0011 | 43 | 74.6 | 255 |
| 7-C | 0.0017 | 66 | 77.3 | 254 |
| 7-D | 0.0023 | 89 | 80.2 | 260 |
| 7-E | 0.0029 | 113 | 73.7 | 284 |
| 7-F | 0.0043 | 167 | inactive | 300 |
| 7-G | 0.0057 | 223 | inactive | 300 |

Illustrative Embodiment X

A catalyst in accord with this invention (Catalyst 8-A) was prepared using a non-alumina support. This support was in the form of 3/16 inch diameter pellets. This support contained 93% by weight silica and 75% by weight alumina and had a surface area of 0.6 m$^2$/g, a median pore diameter of 7 microns as determined by mercury porosimetry, and an apparent porosity of 51% by volume. 80% of its pores had diameters in the range of from 3 to 17 microns. The support was impregnated according to the technique of Illustrative Embodiment I, part A. The weight percent of potassium was 68 ppm (0.0017 gew/kilogram).

A catalyst not in accord with this invention (8-B) was prepared similar to Catalyst 8-A, above, with the exception that no alkali metal was present in the finished catalyst.

When Catalyst 8-A was employed as an ethylene oxidation catalyst in accord with Example I, it gave standard conversion at 256.0° C. and 75.0% selectivity. Catalyst 8-B under the same test conditions gave standard conversion at 257.5° C. and 65.9% selectivity.

We claim as our invention:

1. In the process for the production of ethylene oxide wherein ethylene is contacted in vapor phase with an oxygen-containing gas at ethylene oxide forming conditions at an elevated temperature of from 210° C. to about 285° C. in the presence of a fixed bed of silver metal-containing catalyst, the improvement which comprises employing as said catalyst an article comprising a porous refractory support having deposited on its exterior and pore surfaces from about 2% by weight to about 20% by weight of silver and, coincidentally deposited with silver, a total of from about $3.0 \times 10^{-4}$ gew per kilogram of total catalyst to about $3.2 \times 10^{-3}$ gew per kilogram of total catalyst of alkali metal present in final form on the support in the form of an oxide in which the said oxide consists of the oxide of potassium.

2. The process in accord with claim 1 wherein the amount of alkali metal coincidentally deposited with the silver is in the range from about $5.0 \times 10^{-4}$ to about $2.4 \times 10^{-3}$ gew per kilogram of total catalyst.

3. The process in accord with claim 1 wherein the amount of alkali metal coincidentally deposited with the silver is in the range from about $7.5 \times 10^{-4}$ to about $2.3 \times 10^{-3}$ gew per kilogram of total catalyst.

4. The process in accord with claim 1 wherein the porous refractory support is alpha alumina.

5. In the process for the production of ethylene oxide wherein ethylene is contacted in vapor phase with an oxygen-containing gas at ethylene oxide forming conditions at an elevated temperature of from 210° C. to about 285° C. in the presence of a fixed bed of a silver metal-containing catalyst, the improvement which comprises employing as said catalyst an article consisting essentially of a porous alpha alumina support having a surface area of from about 0.03 m$^2$/g to about 2.0 m$^2$/g and having deposited on its exterior and pore surfaces from about 2% by weight to about 20% by weight of silver and, coincidentally deposited with the silver, a total of from about $3.0 \times 10^{-4}$ gew per kilogram of total catalyst to about $3.2 \times 10^{-3}$ gew per kilogram of total catalyst of alkali metal present in final form on the support in the form of an oxide in which the said oxide consists of the oxide of potassium.

6. The process in accord with claim 5 wherein the surface area of the alpha alumina support is from about 0.1 m$^2$/g to about 2.0 m$^2$/g.

7. The process in accord with claim 6 wherein the silver is present in an amount of from about 3% by weight to about 15% by weight.

8. The process in accord with claim 6 wherein the concentration of said potassium is from about $5.0 \times 10^{-4}$ to about $2.4 \times 10^{-3}$ gew per kilogram of total catalyst.

9. The process in accord with claim 6 wherein the concentration of said potassium is from about $7.5 \times 10^{-4}$ to about $2.3 \times 10^{-3}$ gew per kilogram of total catalyst.

10. In the process for the production of ethylene oxide wherein ethylene is contacted in vapor phase with an oxygen-containing gas at ethylene oxide forming conditions at an elevated temperature of from 210° C. to about 285° C. in the presence of a fixed bed of a silver metal-containing catalyst, the improvement which comprises employing as said catalyst an article comprising a porous support of siliceous composition having a surface area of from about 0.03 $m^2/g$ to about 2.0 $m^2/g$ and having deposited on its exterior and pore surfaces from about 2% by weight to about 20% by weight of silver and, coincidentally deposited with the silver, a total of from about $3.0 \times 10^{-4}$ gew per kilogram of total catalyst to about $3.2 \times 10^{-3}$ gew per kilogram of total catalyst of alkali metal present in final form on the support in the form of an oxide in which the said oxide consists of the oxide of potassium.

11. The process in accord with claim 10 wherein the amount of alkali metal coincidentally deposited with the silver is in the range from about $5.0 \times 10^{-4}$ to about $2.4 \times 10^{-3}$ gew per kilogram of total catalyst.

12. The process in accord with claim 10 wherein the amount of alkali metal coincidentally deposited with the silver is in the range from about $7.5 \times 10^{-4}$ to about $2.3 \times 10^{-3}$ gew per kilogram of total catalyst.

13. In the process for the production of ethylene oxide wherein ethylene is contacted in vapor phase with an oxygen-containing gas at ethylene oxide forming conditions at an elevated temperature of from 210° C. to about 285° C. in the presence of a fixed bed of a silver metal-containing catalyst, the improvement which comprises employing as said catalyst an article prepared by a process which comprises impregnating a porous refractory catalyst support with a solution comprising solvent, silver salt sufficient to deposit on said support from 2% by weight to 20% by weight of silver and salts of one or more higher alkali metals sufficient to deposit on said support a total of from about $3.0 \times 10^{-4}$ gew per kilogram of total catalyst to about $3.2 \times 10^{-3}$ gew per kilogram of total catalyst of alkali metal in the form of a salt in which the said salt consists of the salt of potassium; separating the impregnated support from excess impregnating solution and thereafter reducing the silver salt to silver metal at a temperature of from about 100° C. to about 500° C.

14. The process in accord with claim 13 wherein the amount of alkali metal added to the catalyst support is in the range from about $5.0 \times 10^{-4}$ to about $2.4 \times 10^{-3}$ gew per kilogram of total catalyst.

15. The process in accord with claim 13 wherein the amount of alkali metal added to the catalyst support is in the range from about $7.5 \times 10^{-4}$ to about $2.3 \times 10^{-3}$ gew per kilogram of total catalyst.

16. In the process for the production of ethylene oxide wherein ethylene is contacted in vapor phase with an oxygen-containing gas at ethylene oxide forming conditions at an elevated temperature of from 210° C. to about 285° C. in the presence of a fixed bed of a silver metal-containing catalyst, the improvement which comprises employing as said catalyst an article prepared by a process which comprises:

(a) impregnating a porous refractory catalyst support with solution comprising solvent, silver salt sufficient to deposit from 2% by weight to 20% by weight of silver on said support and salts of alkali metal in which said salt consists of the salt of potassium, sufficient to deposit an amount of the alkali metal in excess of $3.2 \times 10^{-3}$ gew per kilogram of total catalyst on said support;

(b) separating the impregnated support;

(c) reducing the silver salt present on said impregnated support to silver metal at a temperature of from about 100° C. to about 500° C.;

(d) contacting said impregnated support wherein silver is present as silver metal one or more times with an alkanol of 1 or 2 carbon atoms to selectively remove an amount of higher alkali metal present on said impregnated support such that the impregnated support so contacted contains $3.0 \times 10^{-4}$ to $3.2 \times 10^{-3}$ gew of higher alkali metal per kilogram of catalyst present in final form on the support in the form of an oxide in which the said oxide consists of the oxide of potassium;

(e) separating the impregnated support from the alkanol contacting solution and drying to substantially remove the residual alkanol present in and on the impregnated support.

17. The process in accord with claim 16 wherein the amount of alkali metal added to the catalyst support is in the range from about $5.0 \times 10^{-4}$ to about $2.4 \times 10^{-3}$ gew per kilogram of total catalyst.

18. The process in accord with claim 16 wherein the amount of alkali metal added to the catalyst support is in the range from about $7.5 \times 10^{-4}$ to about $2.3 \times 10^{-3}$ gew per kilogram of total catalyst.

19. In the process for the production of ethylene oxide wherein ethylene is contacted in vapor phase with an oxygen-containing gas at ethylene oxide forming conditions at an elevated temperature of from 210° C. to about 285° C. in the presence of a fixed bed of a silver metal-containing catalyst, the improvement which comprises employing as said catalyst an article prepared by a process which comprises:

(a) simultaneously adding to a porous refractory catalyst support from about 3% by weight to about 15% by weight of silver in the form of silver catalyst and from about $3.0 \times 10^{-4}$ gew per kilogram of total catalyst to about $3.2 \times 10^{-3}$ gew per kilogram of total catalyst of alkali metal in the form of water-soluble salts in which said salts consist of salts of potassium, by contacting said support with an alkaline aqueous solution of said silver and higher alkali metal salts; and (b) maintaining the product of step (a) at a temperature of from about 100° C. to about 500° C. in the presence of a reducing agent, thereby converting the silver salts to silver metal.

20. The process in accord with claim 19 wherein the amount of alkali metal added to the catalyst support is in the range from about $5.0 \times 10^{-4}$ to about $2.4 \times 10^{-3}$ gew per kilogram of total catalyst.

21. The process in accord with claim 19 wherein the amount of alkali metal added to the catalyst support is in the range from about $7.5 \times 10^{-4}$ to about $2.3 \times 10^{-3}$ gew per kilogram of total catalyst.

22. The process in accord with claim 19 wherein said alkaline aqueous solution contains an organic amine.

23. The process in accord with claim 22 wherein said silver salts are silver salts of carboxylic acids.

24. The process in accord with claim 19 wherein the porous refractory catalyst support consists essentially of alpha alumina.

25. The process in accord with claim 19 wherein the porous refractory catalyst support is a siliceous solid.

* * * * *